United States Patent [19]

Bollens et al.

[11] Patent Number: 5,753,240
[45] Date of Patent: May 19, 1998

[54] FLUORINATED COMPOUNDS AND COMPOSITIONS COMPRISING THEM

[75] Inventors: Eric Bollens, Saint Maurice; Claude Mahieu, Paris; Michel Philippe, Wissous, all of France

[73] Assignee: L'Oréal, Paris, France

[21] Appl. No.: 531,315

[22] Filed: Sep. 20, 1995

[30] Foreign Application Priority Data

Sep. 21, 1994 [FR] France ................... 94 11266

[51] Int. Cl.⁶ ........................................ A61K 9/00
[52] U.S. Cl. ........................ 424/401; 424/61; 424/63; 424/64; 424/78.03; 424/70.11; 424/DIG. 5; 514/937; 514/944; 560/157; 554/36
[58] Field of Search .................... 424/45, 47, DIG. 1, 424/DIG. 2, 70.11, DIG. 5, 63, 78.03, 61, 489, 401, 64, 439, 451, 464, 52; 560/157; 554/36; 514/937, 944

[56] References Cited

U.S. PATENT DOCUMENTS 5,112,601  5/1992  Sebag et al. ................... 424/61
5,247,121  9/1993  Sebag et al. ................... 560/24

FOREIGN PATENT DOCUMENTS 563 978   10/1993  European Pat. Off. .
647 445   11/1990  France .
93/11103   6/1993  WIPO .

Primary Examiner—Raj Bawa
Attorney, Agent, or Firm—Finnegan, Henderson, Farabow, Garrett, & Dunner, L.L.P.

[57] ABSTRACT

The invention relates to new hydrocarbon compounds containing a fluorinated chain of formula I $$R-O-\underset{\underset{O}{\|}}{C}-NH-(CH_2)_{n'}-\underset{\underset{O}{\|}}{C}-O-(CH_2)_n-R'$$

and to their process of preparation.

The invention also relates to the use of these new compounds as thickening agents, in particular for non-aqueous media, such as cosmetic compositions, and to the cosmetic compositions containing them.

11 Claims, No Drawings

FLUORINATED COMPOUNDS AND COMPOSITIONS COMPRISING THEM

The invention relates to new fluorinated compounds, to their preparation, to their use and to the media and to the compositions comprising them.

Patent Application FR 2,647,445 describes compounds from the family of 11-(N-alkyloxy-carbonyl)aminoundecanoic acids and their non-fluorinated esters, as well as their use as thickening agents, in particular of non-aqueous media. These compounds have the disadvantage of not making it possible to obtain transparent solutions. Moreover, a certain instability, leading to the appearance of crystals in the thickened solutions containing them, is observed.

It is in seeking to remove the disadvantages of these compounds that the inventors have sought for new compounds having at least the same thickening properties. Thus it is that the inventors have developed new compounds containing fluorinated chains which can be used, inter alia, as thickening agents. These compounds can preferably be used with non-aqueous media.

The subject of the invention is therefore fluorinated compounds corresponding to the formula I:

$$R-O-\underset{\underset{O}{\|}}{C}-NH-(CH_2)_{n'}-\underset{\underset{O}{\|}}{C}-O-(CH_2)_n-R'$$

in which

R represents a linear or branched hydrocarbon radical having from 8 to 22 carbon atoms, R' represents a linear or branched perfluorocarbon radical having from 4 to 20 carbon atoms, n ranges from 0 to 4, and n' ranges from 1 to 11.

Hydrocarbon radical is understood to mean any saturated or unsaturated hydrocarbon radical having the required number of carbon atoms.

Perfluorocarbon radical is understood to mean any carbon-containing radical in which all the hydrogen atoms have been replaced by fluorine atoms.

According to a specific embodiment of the invention, R preferably contains from 8 to 16 carbon atoms. According to another embodiment of the invention, R' preferably contains from 4 to 10 carbon atoms. R' is preferably a saturated perfluorocarbon radical.

Mention may be made, as fluorinated compounds of formula I, of:

2-(F-Octyl)ethyl 11-(N-hexadecyloxycarbonyl)-aminoundecanoate;

2-(F-Hexyl)ethyl 11-(N-hexadecyloxycarbonyl)-aminoundecanoate;

2-(F-Octyl)ethyl 2-(N-hexadecyloxycarbonyl)-aminoethanoate;

2-(F-Hexyl)ethyl 2-(N-hexadecyloxycarbonyl)-aminoethanoate;

2-(F-Octyl)ethyl 6-(N-hexadecyloxycarbonyl)-aminohexanoate;

2-(F-Hexyl)ethyl 6-(N-hexadecyloxycarbonyl)-aminohexanoate;

2-(F-Octyl)ethyl 11-(N-docosyloxycarbonyl)-aminoundecanoate;

2-(F-Hexyl)ethyl 11-(N-docosyloxycarbonyl)-aminoundecanoate;

2-(F-Octyl)ethyl 8-(N-hexadecyloxycarbonyl)-aminooctanoate;

2-(F-Hexyl)ethyl 8-(N-hexadecyloxycarbonyl)-aminooctanoate.

A second subject of the invention is a process for the preparation of the compounds of formula I as defined above.

This process is characterized in that a compound from the family of ω-(N-alkyloxycarbonyl)aminoalkylenecarboxylic acids, corresponding to the formula:

$$R-O-\underset{\underset{O}{\|}}{C}-NH-(CH_2)_{n'}-\underset{\underset{O}{\|}}{C}-OH \qquad II$$

is reacted, in a conventional esterification reaction known to a person skilled in the art, in the presence of a solvent and in acid medium, with a fluorinated alcohol corresponding to the formula:

$$R'-(CH_2)_n-OH$$

in which

R represents a linear or branched hydrocarbon radical having from 8 to 22 carbon atoms, R' represents a linear or branched perfluorocarbon radical having from 4 to 20 carbon atoms, n ranges from 0 to 4, and n' ranges from 1 to 11.

According to a specific embodiment of the invention, R preferably contains from 8 to 16 carbon atoms.

According to another embodiment of the invention, R' preferably contains from 4 to 10 carbon atoms. R' is preferably a saturated perfluorocarbon radical.

The solvent used can be a neutral solvent which is conventional for this type of reaction and well known to a person skilled in the art. Mention may be made, for example, of toluene.

A third subject of the invention is another process for the preparation of the compounds of formula I as defined above.

This process is characterized in that an activated derivative from the family of ω(N-alkyloxycarbonyl)-aminoalkylenecarboxylic acids, corresponding to the formula:

$$R-O-\underset{\underset{O}{\|}}{C}-NH-(CH_2)_{n'}-\underset{\underset{O}{\|}}{C}-O-X$$

is reacted, in a conventional esterification reaction known to a person skilled in the art, in the presence of a solvent and optionally in the presence of a basic catalyst, with a fluorinated alcohol corresponding to the formula:

$$R'-(CH_2)_n-OH$$

in which

R represents a linear or branched hydrocarbon radical having from 8 to 22 carbon atoms, R' represents a linear or branched perfluorocarbon radical having from 4 to 20 carbon atoms, n ranges from 0 to 4, n' ranges from 1 to 11, and X represents an activating group such as, in particular, a chlorine, a fluorine, an azole, such as imidazole, or a group OCOOR", in which R" is a hydrocarbon radical having from 2 to 4 carbon atoms.

According to a specific embodiment of the invention, R preferably contains from 8 to 16 carbon atoms.

According to another embodiment of the invention, R' preferably contains from 4 to 10 carbon atoms.

R' is preferably a saturated perfluorocarbon radical.

A fourth subject of the invention relates to the use of the fluorinated compounds of formula I for thickening a non-aqueous medium.

More particularly, they find an application as thickening and/or gelling agents for a liquid fatty phase or for non-aqueous media with a broad polarity spectrum. Media with a broad polarity spectrum is understood to mean both apolar media, such as for example liquid paraffin, and polar media, such as compounds containing an alcohol functional group. As defined herein, oily media is a generic term that includes all liquid oils, such as natural oils, synthetic oils, carbonated oils, hydrofluored or silicone oils, all of which can be used alone or in mixture. The generic term can also include polar oils, such as vegetable oils, or nonpolar oils, such as hydrocarbonated oils, which can also be used alone or in mixtures.

It is possible, for example, to use these thickening agents, and/or the thickened media containing them, in the fields of cosmetics, pharmaceuticals, paints and varnishes, lubricants, fuels and the food industry.

These compounds have remarkable thickening qualities. This property has the consequence of making it possible to use small amounts of this type of compound in the media to be thickened.

These new compounds make it possible most often to obtain transparent thickened media which have a homogeneity which is stable with time.

These new compounds, due to their non-ionic nature, also confer great softness on the compositions comprising them when they are used.

The fluorinated compounds can be used at very low concentrations. They can, in general, be used in amounts from 0.01% to 25%, and preferably from 0.1% and 10%, by weight with respect to the total weight of thickened medium.

The use of these compounds can also make it possible to obtain a gelled medium.

The thickening agent can be a mixture of compounds of formula I, in which R and/or R' are chains of different lengths.

The thickening of the medium can be carried out by completely dissolving the fluorinated compound of formula I, at a temperature ranging from 20° C. to 80° C., and then by allowing the mixture to stand until it is completely thickened.

A fifth subject of the invention relates to a non-aqueous medium comprising at least one compound corresponding to the formula I.

In this medium, the fluorinated compound of formula I can act as thickening agent.

In this medium, the thickening agent can be used at concentrations from 0.01% to 25%, and preferably from 0.1% to 10%, by weight with respect to the total weight of thickened medium.

This medium can be composed of a liquid fatty phase and/or of non-aqueous media with a broad polarity spectrum. This medium can comprise, or be comprised in, cosmetic or pharmaceutical compositions, paints and varnishes, lubricants, fuels or alternatively foodstuffs.

When the non-aqueous medium is, for example, a cosmetic composition, it can comprise the ingredients commonly used in this type of preparation, as defined below.

A sixth subject of the invention relates to a composition comprising at least one non-aqueous medium comprising at least one fluorinated compound corresponding to the formula I.

In this composition, the fluorinated compound of formula I can act as a thickening agent for the non-aqueous medium.

This composition may be utilized in cosmetics, pharmaceuticals, paints and varnishes, lubricants, fuels or alternatively the food industry. In cosmetics or in pharmaceuticals, this composition can, inter alia, be provided in the form of sticks, milks or varnishes.

This composition can include the ingredients commonly used in cosmetics or in pharmaceuticals for this type of preparation. Thus, they can include at least one additive chosen from fatty alcohols, thickeners, fatty acid esters, esters of fatty acids and of glycerol, silicones (volatile or non-volatile, functionalized or non-functionalized), surface-active agents, fragrances, preservatives, sunscreens, proteins, vitamins, polymers, organic or inorganic oils and any other additive conventionally used in the cosmetic or pharmaceutical fields.

All these compositions are prepared according to the usual methods known to a person skilled in the art.

Examples of the preparation of fluorinated compounds corresponding to the formula I, as well as examples of compositions comprising them, will now be given by way of illustration. These examples in no way limit the scope of the invention.

EXAMPLE 1

Synthesis of 2-(F-octyl)ethyl 11-(N-hexadecyloxycarbonyl)aminoundecanoate

The following are introduced into a 1 litre reactor equipped with a Dean and Stark apparatus 39 g (84 mmol) of 2-(F-octyl)ethanol*

37 g (80 mmol) of 11-(N-hexadecyloxycarbonyl)-aminoundecanoic acid 440 g of toluene 2.25 g of para-toluenesulphonic acid.

The mixture is brought to reflux of the solvent for 16 hours. The solution is concentrated in order to obtain a white solid which is filtered off and recrystallized from diisopropyl ether.

38 g (41.5 mmol) of 2-(F-octyl)ethyl 11-(N-hexadecyloxycarbonyl)aminoundecanoate are thus obtained in the form of a white solid, which corresponds to a yield of 52%.

Analysis

Melting point: 98° C. (Mettler FP89)

TLC: Silica gel 60, eluent $CH_2Cl_2$: $R_f=0.6$.

$^{13}C$ N.M.R. spectrum: conforms

Mass spectrum: conforms

Elemental analysis

|  | % C | % H | % N | % F |
| --- | --- | --- | --- | --- |
| Theory | 49.83 | 6.38 | 1.53 | 35.27 |
| Experimental | 49.95 | 6.36 | 1.50 | 35.25 |

Analysis confirms that the expected product has been obtained.

*: marketed by Atochem under the name of Foralkyl EOH 8

EXAMPLE 2

Synthesis of 2-(F-hexyl)ethyl 11-(N-hexadecyloxycarbonyl)aminoundecanoate

The following are introduced into a 0.5 litre reactor equipped with a Dean and Stark apparatus:

8.0 g (22 mmol) of 2-(F-hexyl)ethanol*

9.38 g (20 mmol) of 11-(N-hexadecyloxycarbonyl)-aminoundecanoic acid 240 g of toluene 6 g of para-toluenesulphonic acid.

The mixture is brought to reflux of the solvent for 16 hours. The solution is concentrated in order to obtain a residue which is taken up in the minimum amount of dichloromethane and chromatographed on a column of silica gel.

9.5 g (11.6 mmol) of 2-(F-hexyl)ethyl 11-(N-hexadecyloxycarbonyl)aminoundecanoate are finally obtained, for a yield of 58%.

Analysis

Melting point: 86.9° C. (Mettler FP89)

TLC: Silica gel 60, eluent $CHCl_3$: $R_f$=0.2.

$^{13}C$ N.M.R. spectrum: conforms

Mass spectrum: conforms

Elemental analysis:

|  | % C | % H | % N | % F |
|---|---|---|---|---|
| Theory | 53.00 | 7.17 | 1.72 | 30.27 |
| Experimental | 53.53 | 7.38 | 1.87 | 29.52 |

Analysis confirms that the expected product has been obtained.

*: marketed by Atochem under the name of Foralkyl EOH 8

EXAMPLE 3

Synthesis of 2-(F-octyl)ethyl 2-(N-hexadecyloxycarbonyl) aminoethanoate

Procedure:

16.7 g (0.036 mol) of 2-(F-octyl)ethanol, 10.31 g (0.03 mol) of N-(hexadecyloxycarbonyl)glycine and 90 ml of toluene, in the presence of 0.86 g of para-toluenesulphonic acid, are introduced into a 250 ml round bottom flask equipped with a Dean and Stark apparatus surmounted by a reflux condenser. The reaction medium is heated for 16 hours at reflux of the toluene (130° C.). 10 g of silica 60H are added at 80° C. and this temperature is maintained for 5 min and then the mixture is filtered on sintered glass No. 4 and washed with 30 ml of hot toluene. The filtrate sets solid in the vacuum flask; it is filtered on sintered glass No. 4, dried under vacuum and recrystallized from 50 ml of isopropyl ether; the product obtained is a white powder; m=16 g; yield=68%.

Analyses:

M.p. (Mettler PF85): 77° C.

TLC: Silica gel 60, eluent $CH_2Cl_2$, $I_2$ visualization, $R_f$=0.27

$^1H$ N.M.R. spectrum: conforms

Elemental analysis:

|  | % C | % H | % N | % F |
|---|---|---|---|---|
| Theory | 44.11 | 5.11 | 1.77 | 40.9 |
| Experimental | 43.5 | 5.21 | 1.72 | 40.88 |

Analysis confirms that the expected product has been obtained.

EXAMPLE 4

Synthesis of 2-(F-octyl)ethyl 6-(N-hexa-decyloxycarbonyl) aminohexanoate

Procedure:

14 g (0.03 mol) of 2-(F-octyl)ethanol, 12 g (0.03 mol) of 6-(hexadecyloxycarbonylamino)hexanoic acid and 90 ml of toluene, in the presence of 1.2 g of para-toluenesulphonic acid, are introduced into a 250 ml round bottom flask equipped with a Dean and Stark apparatus surmounted by a reflux condenser. The reaction mixture is brought to reflux of the toluene (130° C.) for 16 h. Then, ⅓ of the toluene is evaporated on a rotary evaporator and 10 g of silica 60 H are added to the round bottom flask, the whole mixture is heated for 5 min at 80° C., then filtered on sintered glass No. 4 and rinsed with 30 ml of toluene at 80° C. The filtrate crystallizes in the vacuum flask and, after returning completely to room temperature, the precipitate is filtered in turn on sintered glass No. 4. The white solid obtained is dried under vacuum and then recrystallized from 50 ml of isopropyl ether.

m=16.5 g; yield=65%

Analyses:

M.p. (Mettler FP85): 86° C.

TLC: Silica gel 60, eluent $CH_2Cl_2$, $I_2$ visualization, $R_f$=0.42

$^1H$ and $^{13}C$ N.M.R. spectra: conform

Elemental analysis:

|  | % C | % H | % O | % F |
|---|---|---|---|---|
| Theory | 46.87 | 5.72 | 1.66 | 38.19 |
| Experimental | 46.97 | 5.86 | 1.72 | 38.22 |

Analysis confirms that the expected product has been obtained.

EXAMPLE 5

Synthesis of 2-(F-octyl)ethyl 11-(N-docosyloxycarbonyl) aminoundecanoate

Procedure:

9.28 g (0.02 mol) of 2-(F-octyl)ethanol, 11.1 g (0.02 mol) of 11-(hexadecyloxycarbonylamino)-undecanoic acid and 60 ml of toluene, in the presence of 0.57 g of para-toluenesulphonic acid, are introduced into a 250 ml round bottom flask equipped with a Dean and Stark apparatus surmounted by a reflux condenser. The reaction medium is heated for 16 hours at 130° C. 6 g of silica 60H are then added at 80° C., this temperature is maintained for 5 min and then the mixture is filtered on sintered glass No. 4 and rinsed with 20 ml of hot toluene. The filtrate crystallizes in the vacuum flask and is filtered on sintered glass No. 4, dried under vacuum and recrystallized from 45 ml of isopropyl ether.

m=15 g of a white powder; yield: 77%

Analyses:

M.p. (Mettler FP85): 97° C.

TLC: Silica gel 60, eluent $CH_2Cl_2$, $I_2$ visualization, $R_f$=0.56

$^{13}C$ N.M.R. spectrum: conforms

Elemental analysis:

|  | % C | % H | % N | % F |
|---|---|---|---|---|
| Theory | 52.85 | 7.06 | 1.4 | 32.3 |
| Experimental | 54 | 7.69 | 1.42 | 31.35 |

Analysis confirms that the expected product has been obtained.

EXAMPLE 6

Synthesis of 2-(F-octyl)ethyl 8-(N-hexadecyloxycarbonyl) aminooctanoate

Procedure:

8.65 g (0.02 mol) of 2-(F-octyl)ethanol, 9.28 g (0.02 mol) of 6-(hexadecyloxycarbonylamino)-octanoic acid, 60 ml of toluene and 0.57 g of para-toluenesulphonic acid are introduced into a 250 ml round bottom flask equipped with a Dean and Stark apparatus surmounted by a reflux condenser. The reaction medium is heated for 16 hours at reflux of the toluene (130° C.). The toluene is then concentrated by a third and then 6 g of silica 60H are added to the round bottom flask. The whole mixture is heated for 5 min at 80° C. and then filtered on sintered glass No. 4 and rinsed with 20 ml of hot toluene. The filtrate crystallizes in the vacuum flask and, after returning to room temperature, the precipitate is filtered on sintered glass No. 4. The white solid obtained (22.6 g) is dried under vacuum and then recrystallized with 100 ml of isopropyl ether. The product obtained is a white powder.

m=10.9 g; yield: 63%

Analyses:

M.p. (Mettler PF85): 92° C.

TLC: Silica gel 60, eluent $CH_2Cl_2$, $I_2$ visualization. $R_f$=0.47

$^{13}C$ N.M.R. spectrum: conforms

Elemental analysis:

|  | % C | % H | % N | % F |
|---|---|---|---|---|
| Theory | 48.11 | 6 | 1.6 | 36.96 |
| Experimental | 47.33 | 5.82 | 1.58 | 37.8 |

EXAMPLE 7
Thickening effect of Example 1 on various vehicles

| Example 1 | 1% | 0.5% | 0.2% |
|---|---|---|---|
| Eutanol G | transparent gel | transparent gel | transparent gel |
| Perhydro-squalene | transparent gel | transparent gel | no effect |
| Petroleum jelly | transparent gel | transparent gel | no effect |
| Sunflower | transparent gel | transparent gel | no effect |
| Parleam | transparent gel | transparent gel | no effect |
| Olive oil | transparent gel | transparent gel | no effect |

As is evident, Sunflower refers to Sunflower oil and Parleam refers to Parleam oil. Eutanol G is a tradename for octyldodecanol and is manufactured by Henkel.

This test shows that it is possible, depending on the nature of the oily media to be thickened, to use 2-(F-octyl)ethyl 11-(N-hexadecyloxycarbonyl)aminoundecanoate at extremely low concentrations. Gelled media were thus obtained. These thickened media have shown perfect stability over a period of over 6 months.

EXAMPLE 8
Lipstick

| 2-(F-Octyl)ethyl 11-(N-hexadecyloxycarbonyl)-aminoundecanoate | 1.00% |
|---|---|
| Ozokerite | 14.90% |
| Microcrystalline wax | 4.90% |
| Candelilla wax | 7.40% |
| Jojoba oil | 6.20% |
| Castor oil | 1.20% |
| Liquid lanolin | 18.60% |
| Acetylated lanolin | 9.90% |
| Liquid paraffin | 11.10% |
| Talc | 3.70% |
| Titanium oxide-coated mica | 8.70% |
| D & C Red No. 7 Ca lake | 5.20% |
| D & C Red No. 7 Ba lake | 2.80% |
| FD & C Yellow No. 5 | 1.00% |
| Titanium dioxide | 3.10% |
| Butylated hydroxytoluene | 0.30% |
| Fragrance q.s. for | 100.00% |

This lipstick is characterized by good application properties and good behaviour.

EXAMPLE 9
Foundation cream

| 2-(F-Octyl)ethyl 11-(N-hexadecyloxycarbonyl)-aminoundecanoate | 0.50% |
|---|---|
| Dimethylpolysiloxane | 29.40% |
| Cetyldimethicone copolyol ("Abil EM 90" from Goldschmidt) | 3.00% |
| Water | 57.00% |
| Magnesium sulphate | 0.70% |
| Glycerol | 5.00% |
| Yellow iron oxide | 0.60% |
| Red iron oxide | 0.39% |
| Black iron oxide | 0.11% |
| Titanium dioxide | 2.90% |
| Preservatives q.s. for | 100.00% |

This foundation cream is also characterized by good application properties and good cosmetic behaviour.

We claim:

1. A fluorinated compound of the formula I:

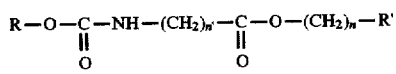

in which R represents a linear or branched hydrocarbon radical having from 8 to 22 carbon atoms, R' represents a linear or branched perfluorocarbon radical having from 4 to 20 carbon atoms, n ranges from 0 to 4, and n' ranges from 1 to 11.

2. The compound according to claim 1, in which R is a linear or branched hydrocarbon radical having from 8 to 16 carbon atoms.

3. The compound according to claim 1, in which R' is a linear or branched perfluorocarbon radical having from 4 to 10 carbon atoms.

4. The compound according to claim 1, in which said compound is 2-(perfluoro-octyl)ethyl 11-(N-hexadecyloxycarbonyl)-aminoundecanoate;

2-(perfluoro-hexyl)ethyl 11-(N-hexadecyloxycarbonyl)-aminoundecanoate;

2-(perfluoro-octyl)ethyl 2-(N-hexadecyloxycarbonyl)-aminoethanoate;

2-(perfluoro-hexyl)ethyl 2-(N-hexadecyloxycarbonyl)-aminoethanoate;

2-(perfluoro-octyl)ethyl 6-(N-hexadecyloxycarbonyl)-aminohexanoate;

2-(perfluoro-hexyl)ethyl 6-(N-hexadecyloxycarbonyl)-aminohexanoate;

2-(perfluoro-octyl)ethyl 11-(N-docosyloxycarbonyl)-aminoundecanoate;

2-(perfluoro-hexyl)ethyl 11-(N-docosyloxycarbonyl)-aminoundecanoate;

2-(perfluoro-octyl)ethyl 8-(N-hexadecyloxycarbonyl)-aminooctanoate; or 2-(perfluoro-hexyl)ethyl 8-(N-hexadecyloxycarbonyl)-aminooctanoate.

5. A non-aqueous medium comprising at least one fluorinated compound of the formula I:

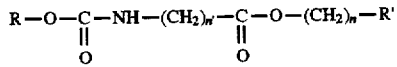

in which R represents a linear or branched hydrocarbon radical having from 8 to 22 carbon atoms, R' represents a linear or branched perfluorocarbon radical having from 4 to 20 carbon atoms, n ranges from 0 to 4, and n' ranges from 1 to 11.

6. A non-aqueous medium comprising an amount effective for thickening said medium of at least one fluorinated compound of the formula I:

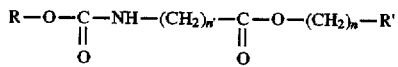

in which R represents a linear or branched hydrocarbon radical having from 8 to 22 carbon atoms, R' represents a linear or branched perfluorocarbon radical having from 4 to 20 carbon atoms, n ranges from 0 to 4, and n' ranges from 1 to 11.

7. The non-aqueous medium according to claim 6, in which said amount of said fluorinated compound of formula I effective for thickening ranges from 0.01% to 25% by weight with respect to the total weight of the medium.

8. The non-aqueous medium according to claim 7, in which said amount of said fluorinated compound of formula I effective for thickening ranges from 0.01% to 10% by weight with respect to the total weight of the medium.

9. A composition comprising the non-aqueous medium according to claim 6.

10. The composition of claim 9, wherein said composition is a cosmetic composition or a pharmaceuticals.

11. The composition of claim 10, wherein said cosmetic composition or pharmaceutical is in the form of an emulsion, a stick, a milk or a varnish.

* * * * *

UNITED STATES PATENT AND TRADEMARK OFFICE
CERTIFICATE OF CORRECTION

PATENT NO. : 5,753,240
DATED      : May 19, 1998
INVENTOR(S) : Eric BOLLENS et al.

It is certified that error appears in the above-indentified patent and that said Letters Patent is hereby corrected as shown below:

<u>IN THE CLAIMS</u>:

Claim 10, col. 10, lines 12, "pharmaceuticals" should read --pharmaceutical--.

Signed and Sealed this

Fourteenth Day of July, 1998

Attest:

BRUCE LEHMAN

*Attesting Officer*         *Commissioner of Patents and Trademarks*